(12) United States Patent
Dransfield

(10) Patent No.: US 8,686,137 B2
(45) Date of Patent: Apr. 1, 2014

(54) HETEROCYCLIC COMPOUNDS AND THEIR USES

(75) Inventor: Paul John Dransfield, San Francisco, CA (US)

(73) Assignee: Amgen Inc., Thousand Oaks, CA (US)

(*) Notice: Subject to any disclaimer, the term of this patent is extended or adjusted under 35 U.S.C. 154(b) by 0 days.

(21) Appl. No.: 13/701,772

(22) PCT Filed: Jun. 30, 2011

(86) PCT No.: PCT/US2011/042531
§ 371 (c)(1),
(2), (4) Date: Dec. 3, 2012

(87) PCT Pub. No.: WO2012/003278
PCT Pub. Date: Jan. 5, 2012

(65) Prior Publication Data
US 2013/0143882 A1    Jun. 6, 2013

Related U.S. Application Data

(60) Provisional application No. 61/360,262, filed on Jun. 30, 2010.

(51) Int. Cl.
C07D 417/14    (2006.01)
A61K 31/5377   (2006.01)

(52) U.S. Cl.
USPC ........................ 544/128; 514/235.2

(58) Field of Classification Search
None
See application file for complete search history.

(56) References Cited

U.S. PATENT DOCUMENTS 6,355,636 B1    3/2002  Wissner et al.
6,384,051 B1    5/2002  Frost et al.

FOREIGN PATENT DOCUMENTS

WO    2010/061180 A1    6/2010

OTHER PUBLICATIONS

Berndt, et al., "The p110δ structure: Mechanisms for selectivity and potency of new PI(3)K inhibitors" Nature Chemical Biology, Jan. 10, 2010 pp. 1-8.
Berndt, et al., "Supplementary Methods and Results The p110δ structure. Mechanisms for selectivity and potency of new PI(3)K inhibitors" Nature Chemical Biology, Jan. 2010 pp. 1-34.
Price, "A Synthesis of Substituted 4-Aminoquinolines" J of Am Chem Soc (1946) pp. 1246-1250, vol. 68.
Boschelli, "Facile preparation of new 4-phenylamino-3-quinolinecarboritrile Src kinase inhibitors via 7-fluoro intermediates: Identification of potent 7-amino analogs", Bioorganic & Medicinal Chem (2008) pp. 405-412, vol. 16 No. 1.
Crespo, "Redesigning kinase inhibitors to enhance specificity", J of Medicinal Chem (2008) pp. 4890-4898, vol. 51, No. 16.

Primary Examiner — Janet L Andres
Assistant Examiner — Timothy R Rozof
(74) Attorney, Agent, or Firm — Richard v. Person

(57) ABSTRACT

Compounds having the structure which are selective inhibitors of P13K (phosphatidylinositol 3-kinase-delta), for the treatment of general inflammation, arthritis, rheumatic diseases, osteoarthritis inflammatory bowel disorders, inflammatory eye disorders, inflammatory or unstable bladder disorders, psoriasis, skin complaints with inflammatory components, chronic inflammatory conditions.

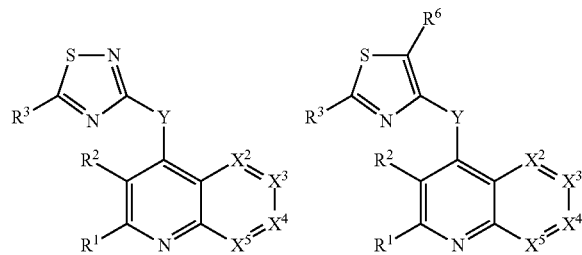

2 Claims, No Drawings

HETEROCYCLIC COMPOUNDS AND THEIR USES

This application claims the benefit of U.S. Provisional Application No. 61/360,262, filed Jun. 30, 2010, which is hereby incorporated by reference.

The present invention relates generally to phosphatidylinositol 3-kinase (PI3K) enzymes, and more particularly to selective inhibitors of PI3K activity and to methods of using such materials.

BACKGROUND OF THE INVENTION

Cell signaling via 3'-phosphorylated phosphoinositides has been implicated in a variety of cellular processes, e.g., malignant transformation, growth factor signaling, inflammation, and immunity (see Rameh et al., J. Biol Chem, 274: 8347-8350 (1999) for a review). The enzyme responsible for generating these phosphorylated signaling products, phosphatidylinositol 3-kinase (PI 3-kinase; PI3K), was originally identified as an activity associated with viral oncoproteins and growth factor receptor tyrosine kinases that phosphorylates phosphatidylinositol (PI) and its phosphorylated derivatives at the 3'-hydroxyl of the inositol ring (Panayotou et al., Trends Cell Biol 2:358-60 (1992)).

The levels of phosphatidylinositol-3,4,5-triphosphate (PIP3), the primary product of PI 3-kinase activation, increase upon treatment of cells with a variety of stimuli. This includes signaling through receptors for the majority of growth factors and many inflammatory stimuli, hormones, neurotransmitters and antigens, and thus the activation of PI3Ks represents one, if not the most prevalent, signal transduction events associated with mammalian cell surface receptor activation (Cantley, Science 296:1655-1657 (2002); Vanhaesebroeck et al. Annu Rev. Biochem, 70: 535-602 (2001)). PI 3-kinase activation, therefore, is involved in a wide range of cellular responses including cell growth, migration, differentiation, and apoptosis (Parker et al., Current Biology, 5:577-99 (1995); Yao et al., Science, 267:2003-05 (1995)). Though the downstream targets of phosphorylated lipids generated following PI 3-kinase activation have not been fully characterized, it is known that pleckstrin-homology (PH) domain- and FYVE-finger domain-containing proteins are activated when binding to various phosphatidylinositol lipids (Sternmark et al., J Cell Sci, 112:4175-83 (1999); Lemmon et al., Trends Cell Biol, 7:237-42 (1997)). Two groups of PH-domain containing PI3K effectors have been studied in the context of immune cell signaling, members of the tyrosine kinase TEC family and the serine/threonine kinases of to AGC family. Members of the Tec family containing PH domains with apparent selectivity for PtdIns (3,4,5)P$_3$ include Tec, Btk, Itk and Etk. Binding of PH to PIP$_3$ is critical for tyrosine kinase activity of the Tec family members (Schaeffer and Schwartzberg, Curr. Opin. Immunol. 12: 282-288 (2000)) AGC family members that are regulated by PI3K include the phosphoinositide-dependent kinase (PDK1), AKT (also termed PKB) and certain isoforms of protein kinase C(PKC) and S6 kinase. There are three isoforms of AKT and activation of AKT is strongly associated with PI3K-dependent proliferation and survival signals. Activation of AKT depends on phosphorylation by PDK1, which also has a 3-phosphoinositide-selective PH domain to recruit it to the membrane where it interacts with AKT. Other important PDK1 substrates are PKC and S6 kinase (Deane and Fruman, Annu Rev. Immunol. 22_563-598 (2004)). In vitro, some isoforms of protein kinase C (PKC) are directly activated by PIP3. (Burgering et al., Nature, 376:599-602 (1995)).

Presently, the PI 3-kinase enzyme family has been divided into three classes based on their substrate specificities. Class I PI3Ks can phosphorylate phosphatidylinositol (PI), phosphatidylinositol-4-phosphate, and phosphatidyl-inositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidyl-inositol-4-phosphate, whereas Class III PI3Ks can only phosphorylate PI.

The initial purification and molecular cloning of PI 3-kinase revealed that it was a heterodimer consisting of p85 and p110 subunits (Otsu et al., Cell, 65:91-104 (1991); Hiles et al., Cell, 70:419-29 (1992)). Since then, four distinct Class I PI3Ks have been identified, designated PI3K α, β, δ, and γ, each consisting of a distinct 110 kDa catalytic subunit and a regulatory subunit. More specifically, three of the catalytic subunits, i.e., p110α, p110β and p110δ, each interact with the same regulatory subunit, p85; whereas p110γ interacts with a distinct regulatory subunit, p101. As described below, the patterns of expression of each of these PI3Ks in human cells and tissues are also distinct. Though a wealth of information has been accumulated in recent past on the cellular functions of PI 3-kinases in general, the roles played by the individual isoforms are not fully understood.

Cloning of bovine p110α has been described. This protein was identified as related to the *Saccharomyces cerevisiae* protein: Vps34p, a protein involved in vacuolar protein processing. The recombinant p110α product was also shown to associate with p85α, to yield a PI3K activity in transfected COS-1 cells. See Hiles et al., Cell, 70, 419-29 (1992).

The cloning of a second human p110 isoform, designated p110β, is described in Hu et al., Mol Cell Biol, 13:7677-88 (1993). This isoform is said to associate with p85 in cells, and to be ubiquitously expressed, as p110β mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Such wide expression suggests that this isoform is broadly important in signaling pathways.

Identification of the p110δ isoform of PI 3-kinase is described in Chantry et al., J Biol Chem, 272:19236-41 (1997). It was observed that the human p110δ isoform is expressed in a tissue-restricted fashion. It is expressed at high levels in lymphocytes and lymphoid tissues and has been shown to play a key role in PI 3-kinase-mediated signaling in the immune system (Al-Alwan etl al. JI 178: 2328-2335 (2007); Okkenhaug et al JI, 177: 5122-5128 (2006); Lee et al. PNAS, 103: 1289-1294 (2006)). P110δ has also been shown to be expressed at lower levels in breast cells, melanocytes and endothelial cells (Vogt et al. Virology, 344: 131-138 (2006) and has since been implicated in conferring selective migratory properties to breast cancer cells (Sawyer et al. Cancer Res. 63:1667-1675 (2003)). Details concerning the P110δ isoform also can be found in U.S. Pat. Nos. 5,858,753; 5,822,910; and 5,985,589. See also, Vanhaesebroeck et al., Proc Nat. Acad Sci USA, 94:4330-5 (1997), and international publication WO 97/46688.

In each of the PI3Kα, β, and δ subtypes, the p85 subunit acts to localize PI 3-kinase to the plasma membrane by the interaction of its SH2 domain with phosphorylated tyrosine residues (present in an appropriate sequence context) in target proteins (Rameh et al., Cell, 83:821-30 (1995)). Five isoforms of p85 have been identified (p85α, p85β, p55γ, p55α and p50α) encoded by three genes. Alternative transcripts of Pik3r1 gene encode the p85α, p55 α and p50α proteins (Deane and Fruman, Annu Rev. Immunol. 22: 563-598

(2004)). p85α is ubiquitously expressed while p8513, is primarily found in the brain and lymphoid tissues (Volinia et al., Oncogene, 7:789-93 (1992)). Association of the p85 subunit to the PI 3-kinase p110α, β, or δ catalytic subunits appears to be required for the catalytic activity and stability of these enzymes. In addition, the binding of Ras proteins also upregulates PI 3-kinase activity.

The cloning of p110γ revealed still further complexity within the PI3K family of enzymes (Stoyanov et al., Science, 269:690-93 (1995)). The p110γ isoform is closely related to p110α and p110β (45-48% identity in the catalytic domain), but as noted does not make use of p85 as a targeting subunit. Instead, p110γ binds a p101 regulatory subunit that also binds to the βγ subunits of heterotrimeric G proteins. The p101 regulatory subunit for PI3 Kgamma was originally cloned in swine, and the human ortholog identified subsequently (Krugmann et al., J Biol Chem, 274:17152-8 (1999)). Interaction between the N-terminal region of p101 with the N-terminal region of p110γ is known to activate PI3Kγ through Gβγ. Recently, a p101-homologue has been identified, p84 or p87$^{PIKAP}$ (PI3Kγ adapter protein of 87 kDa) that binds p110γ (Voigt et al. JBC, 281: 9977-9986 (2006), Suire et al. Curr. Biol. 15: 566-570 (2005)). p87$^{PIKAP}$ is homologous to p101 in areas that bind p110γ and Gβγ and also mediates activation of p110γ downstream of G-protein-coupled receptors. Unlike p101, p87$^{PIKAP}$ is highly expressed in the heart and may be crucial to PI3Kγ cardiac function.

A constitutively active PI3K polypeptide is described in international publication WO 96/25488. This publication discloses preparation of a chimeric fusion protein in which a 102-residue fragment of p85 known as the inter-SH2 (iSH2) region is fused through a linker region to the N-terminus of murine p110. The p85 iSH2 domain apparently is able to activate PI3K activity in a manner comparable to intact p85 (Klippel et al., Mol Cell Biol, 14:2675-85 (1994)).

Thus, PI 3-kinases can be defined by their amino acid identity or by their activity. Additional members of this growing gene family include more distantly related lipid and protein kinases including Vps34 TOR1, and TOR2 of *Saccharomyces cerevisiae* (and their mammalian homologs such as FRAP and mTOR), the ataxia telangiectasia gene product (ATR) and the catalytic subunit of DNA-dependent protein kinase (DNA-PK). See generally, Hunter, Cell, 83:1-4 (1995).

PI 3-kinase is also involved in a number of aspects of leukocyte activation. A p85-associated PI 3-kinase activity has been shown to physically associate with the cytoplasmic domain of CD28, which is an important costimulatory molecule for the activation of T-cells in response to antigen (Pages et al., Nature, 369:327-29 (1994); Rudd, Immunity, 4:527-34 (1996)). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al., Science, 251:313-16 (1991)). Mutation of CD28 such that it can no longer interact with PI 3-kinase leads to a failure to initiate IL2 production, suggesting a critical role for PI 3-kinase in T cell activation.

Specific inhibitors against individual members of a family of enzymes provide invaluable tools for deciphering functions of each enzyme. Two compounds, LY294002 and wortmannin, have been widely used as PI 3-kinase inhibitors. These compounds, however, are nonspecific PI3K inhibitors, as they do not distinguish among the four members of Class I PI 3-kinases. For example, the IC$_{50}$ values of wortmannin against each of the various Class I PI 3-kinases are in the range of 1-10 nM. Similarly, the IC$_{50}$ values for LY294002 against each of these PI 3-kinases is about 1 μM (Froman et al., Ann Rev Biochem, 67:481-507 (1998)). Hence, the utility of these compounds in studying the roles of individual Class I PI 3-kinases is limited.

Based on studies using wortmannin, there is evidence that PI 3-kinase function also is required for some aspects of leukocyte signaling through G-protein coupled receptors (Thelen et al., Proc Natl Acad Sci USA, 91:4960-64 (1994)). Moreover, it has been shown that wortmannin and LY294002 block neutrophil migration and superoxide release. However, inasmuch as these compounds do not distinguish among the various isoforms of PI3K, it remains unclear from these studies which particular PI3K isoform or isoforms are involved in these phenomena and what functions the different Class I PI3K enzymes perform in both normal and diseased tissues in general. The co-expression of several PI3K isoforms in most tissues has confounded efforts to segregate the activities of each enzyme until recently.

The separation of the activities of the various PI3K isozymes has been advanced recently with the development of genetically manipulated mice that allowed the study of isoform-specific knock-out and kinase dead knock-in mice and the development of more selective inhibitors for some of the different isoforms. P110α and p110β knockout mice have been generated and are both embryonic lethal and little information can be obtained from these mice regarding the expression and function of p110 alpha and beta (Bi et al. Mamm. Genome, 13:169-172 (2002); Bi et al. J. Biol. Chem. 274: 10963-10968 (1999)). More recently, p110α kinase dead knock in mice were generated with a single point mutation in the DFG motif of the ATP binding pocket (p110αD$^{933A}$) that impairs kinase activity but preserves mutant p110α kinase expression. In contrast to knock out mice, the knockin approach preserves signaling complex stoichiometry, scaffold functions and mimics small molecule approaches more realistically than knock out mice. Similar to the p110α KO mice, p110αD$^{933A}$ homozygous mice are embryonic lethal. However, heterozygous mice are viable and fertile but display severely blunted signaling via insulin-receptor substrate (IRS) proteins, key mediators of insulin, insulin-like growth factor-1 and leptin action. Defective responsiveness to these hormones leads to hyperinsulinaemia, glucose intolerance, hyperphagia, increase adiposity and reduced overall growth in heterozygotes (Foukas, et al. Nature, 441: 366-370 (2006)). These studies revealed a defined, non-redundant role for p110α as an intermediate in IGF-1, insulin and leptin signaling that is not substituted for by other isoforms. We will have to await the description of the p110β kinase-dead knock in mice to further understand the function of this isoform (mice have been made but not yet published; Vanhaesebroeck).

P110γ knock out and kinase-dead knock in mice have both been generated and overall show similar and mild phenotypes with primary defects in migration of cells of the innate immune system and a defect in thymic development of T cells (Li et al. Science, 287: 1046-1049 (2000), Sasaki et al. Science, 287: 1040-1046 (2000), Patrucco et al. Cell, 118: 375-387 (2004)).

Similar to p110γ, PI3K delta knock out and kinase-dead knock-in mice have been made and are viable with mild and like phenotypes. The p110δ$^{D910A}$ mutant knock in mice demonstrated an important role for delta in B cell development and function, with marginal zone B cells and CD5+B1 cells nearly undetectable, and B- and T cell antigen receptor signaling (Clayton et al. J. Exp.Med. 196:753-763 (2002); Okkenhaug et al. Science, 297: 1031-1034 (2002)). The p110δ$^{D910A}$ mice have been studied extensively and have elucidated the diverse role that delta plays in the immune system. T cell dependent and T cell independent immune responses are severely attenuated in p110δ$^{D910A}$ and secretion of TH1 (INF-γ) and TH2 cytokine (IL-4, IL-5) are impaired (Okkenhaug et al. J. Immunol. 177: 5122-5128 (2006)). A human patient with a mutation in p110δ has also recently been described. A taiwanese boy with a primary B cell immunodeficiency and a gamma-hypoglobulinemia of previously unkown aetiology presented with a single base-pair substitution, m.3256G to A in codon 1021 in exon 24 of p110δ. This mutation resulted in a mis-sense amino acid substitution (E to K) at codon 1021, which is located in the highly conserved catalytic domain of p110δ protein. The patient has no other identified mutations and his phenotype is consistent with p110δ deficiency in mice as far as studied. (Jou et al. Int. J. Immunogenet. 33: 361-369 (2006)).

Isoform-selective small molecule compounds have been developed with varying success to all Class I PI3 kinase isoforms (Ito et al. J. Pharm. Exp. Therapeut., 321:1-8 (2007)). Inhibitors to alpha are desirable because mutations in p110α have been identified in several solid tumors; for example, an amplification mutation of alpha is associated with 50% of ovarian, cervical, lung and breast cancer and an activation mutation has been described in more than 50% of bowel and 25% of breast cancers (Hennessy et al. Nature Reviews, 4: 988-1004 (2005)). Yamanouchi has developed a compound YM-024 that inhibits alpha and delta equi-potently and is 8- and 28-fold selective over beta and gamma respectively (Ito et al. J. Pharm. Exp. Therapeut., 321:1-8 (2007)).

P110β is involved in thrombus formation (Jackson et al. Nature Med. 11: 507-514 (2005)) and small molecule inhibitors specific for this isoform are thought after for indication involving clotting disorders (TGX-221: 0.007 uM on beta; 14-fold selective over delta, and more than 500-fold selective over gamma and alpha) (Ito et al. J. Pharm. Exp. Therapeut., 321:1-8 (2007)).

Selective compounds to p110γ are being developed by several groups as immunosuppressive agents for autoimmune disease (Rueckle et al. Nature Reviews, 5: 903-918 (2006)). Of note, AS 605240 has been shown to be efficacious in a mouse model of rheumatoid arthritis (Camps et al. Nature Medicine, 11: 936-943 (2005)) and to delay onset of disease in a model of systemic lupus erythematosis (Barber et al. Nature Medicine, 11: 933-935 (205)).

Delta-selective inhibitors have also been described recently. The most selective compounds include the quinazolinone purine inhibitors (PIK39 and IC87114). IC87114 inhibits p110δ in the high nanomolar range (triple digit) and has greater than 100-fold selectivity against p110α, is 52 fold selective against p110β but lacks selectivity against p110γ (approx. 8-fold). It shows no activity against any protein kinases tested (Knight et al. Cell, 125: 733-747 (2006)). Using delta-selective compounds or genetically manipulated mice (p110δ$^{D910A}$) it was shown that in addition to playing a key role in B and T cell activation, delta is also partially involved in neutrophil migration and primed neutrophil respiratory burst and leads to a partial block of antigen-IgE mediated mast cell degranulation (Condliffe et al. Blood, 106: 1432-1440 (2005); Ali et al. Nature, 431: 1007-1011 (2002)). Hence p110δ is emerging as an important mediator of many key inflammatory responses that are also known to participate in aberrant inflammatory conditions, including but not limited to autoimmune disease and allergy. To support this notion, there is a growing body of p110δ target validation data derived from studies using both genetic tools and pharmacologic agents. Thus, using the delta-selective compound IC 87114 and the p110δ$^{D910A}$ mice, Ali et al. (Nature, 431: 1007-1011 (2002)) have demonstrated that delta plays a critical role in a murine model of allergic disease. In the absence of functional delta, passive cutaneous anaphylaxis (PCA) is significantly reduced and can be attributed to a reduction in allergen-IgE induced mast cell activation and degranulation. In addition, inhibition of delta with IC 87114 has been shown to significantly ameliorate inflammation and disease in a murine model of asthma using ovalbumin-induced airway inflammation (Lee et al. FASEB, 20: 455-465 (2006). These data utilizing compound were corroborated in p110δ$^{D910A}$ mutant mice using the same model of allergic airway inflammation by a different group (Nashed et al. Eur. J. Immunol. 37:416-424 (2007)).

There exists a need for further characterization of PI3Kδ function in inflammatory and auto-immune settings. Furthermore, our understanding of PI3Kδ requires further elaboration of the structural interactions of p110δ, both with its regulatory subunit and with other proteins in the cell. There also remains a need for more potent and selective or specific inhibitors of PI3K delta, in order to avoid potential toxicology associated with activity on isozymes p110 alpha (insulin signaling) and beta (platelet activation). In particular, selective or specific inhibitors of PI3Kδ are desirable for exploring the role of this isozyme further and for development of superior pharmaceuticals to modulate the activity of the isozyme.

SUMMARY

The present invention comprises a new class of compounds having the general formula

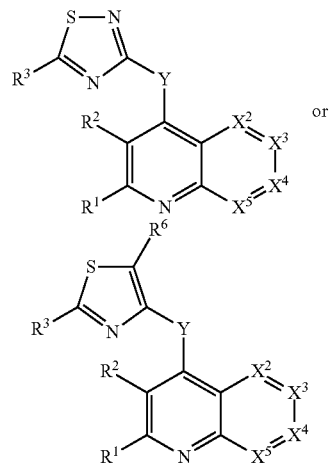

which are useful to inhibit the biological activity of human PI3Kδ. Another aspect of the invention is to provide compounds that inhibit PI3Kδ selectively while having relatively low inhibitory potency against the other PI3K isoforms. Another aspect of the invention is to provide methods of characterizing the function of human PI3Kδ. Another aspect of the invention is to provide methods of selectively modulating human PI3Kδ activity, and thereby promoting medical treatment of diseases mediated by PI3Kδ dysfunction. Other aspects and advantages of the invention will be readily apparent to the artisan having ordinary skill in the art.

DETAILED DESCRIPTION

One aspect of the present invention relates to compounds having the structure:

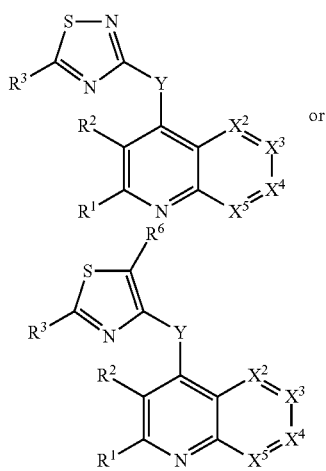

or any pharmaceutically-acceptable salt thereof, wherein:

X² is C(R⁴) or N;
X³ is C(R⁵) or N;
X⁴ is C(R⁵) or N;
X⁵ is C(R⁴) or N; wherein no more than two of X², X³, X⁴ and X⁵ are N;
Y is NR⁷, CRᵃRᵃ, S or O;
n is 0, 1, 2 or 3;
R¹ is selected from H, halo, $C_{1-6}$alk, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC$_{2-6}$alkNRᵃRᵃ, —OC$_{2-6}$alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC$_{2-6}$alkNRᵃRᵃ, —NRᵃC$_{2-6}$alkORᵃ, —NRᵃC$_{2-6}$alkCO₂Rᵃ, —NRᵃC$_{2-6}$alkSO₂Rᵇ, —CH₂C(=O)Rᵃ, —CH₂C(=O)ORᵃ, —CH₂C(=O)NRᵃRᵃ, —CH₂C(=NRᵃ)NRᵃRᵃ, —CH₂ORᵃ, —CH₂OC(=O)Rᵃ, —CH₂C(=O)NRᵃRᵃ, —CH₂C(=O)N(Rᵃ)S(=O)₂Rᵃ, —CH₂OC$_{2-6}$alkNRᵃRᵃ, —CH₂OC$_{2-6}$alkORᵃ, —CH₂SRᵃ, —CH₂S(=O)Rᵃ, —CH₂S(=O)₂Rᵇ, —CH₂S(=O)₂NRᵃRᵃ, —CH₂S(=O)₂N(Rᵃ)C(=O)Rᵃ, —CH₂S(=O)₂N(Rᵃ)C(=O)ORᵃ, —CH₂S(=O)₂N(Rᵃ)C(=O)NRᵃRᵃ, —CH₂NRᵃRᵃ, —CH₂N(Rᵃ)C(=O)Rᵃ, —CH₂N(Rᵃ)C(=O)ORᵃ, —CH₂N(Rᵃ)C(=O)NRᵃRᵃ, —CH₂N(Rᵃ)C(=NRᵃ)NRᵃRᵃ, —CH₂N(Rᵃ)S(=O)₂Rᵃ, —CH₂N(Rᵃ)S(=O)₂NRᵃRᵃ, —CH₂NRᵃC$_{2-6}$alkNRᵃRᵃ, —CH₂NRᵃC$_{2-6}$alkORᵃ, —CH₂NRᵃC$_{2-6}$alkCO₂Rᵃ and —CH₂NRᵃC$_{2-6}$alkSO₂Rᵇ; or R¹ is a direct-bonded, $C_{1-4}$alk-linked, OC$_{1-2}$alk-linked, $C_{1-2}$alkO-linked, N(Rᵃ)-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC$_{2-6}$alkNRᵃRᵃ, —OC$_{2-6}$alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)S(=O)₂NRᵃRᵃ, —NRᵃC$_{2-6}$alkNRᵃRᵃ and —NRᵃC$_{2-6}$alkORᵃ, wherein the available carbon atoms of the ring are additionally substituted by 0, 1 or 2 oxo or thioxo groups, and wherein the ring is additionally substituted by 0 or 1 directly bonded, SO₂ linked, C(=O) linked or CH₂ linked group selected from phenyl, pyridyl, pyrimidyl, morpholino, piperazinyl, piperadinyl, pyrrolidinyl, cyclopentyl, cyclohexyl all of which are further substituted by 0, 1, 2 or 3 groups selected from halo, $C_{1-6}$alk, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —SRᵃ, —S(=O)Rᵃ, —S(=O)₂Rᵃ, —S(=O)₂NRᵃRᵃ, —NRᵃRᵃ, and —N(Rᵃ)C(=O)Rᵃ;

R² is selected from halo, $C_{1-6}$alk, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC$_{2-6}$alkNRᵃRᵃ, —OC$_{2-6}$alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC$_{2-6}$alkNRᵃRᵃ and —NRᵃC$_{2-6}$alkORᵃ;

R³ is selected from a saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 R² substituents, and the ring is additionally substituted by 0, 1, 2 or 3 substituents independently selected from halo, $C_{1-6}$alk, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, —OC(=O)N(Rᵃ)S(=O)₂Rᵃ, —OC$_{2-6}$alkNRᵃRᵃ, —OC$_{2-6}$alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC$_{2-6}$alkNRᵃRᵃ and —NRᵃC$_{2-6}$alkORᵃ; or R³ is selected from halo, $C_{1-6}$alk, $C_{1-4}$haloalk, cyano, nitro, —C(=O)Rᵃ, —C(=O)ORᵃ, —C(=O)NRᵃRᵃ, —C(=NRᵃ)NRᵃRᵃ, —ORᵃ, —OC(=O)Rᵃ, —OC(=O)NRᵃRᵃ, C(=O)N(Rᵃ)S(=O)₂Rᵃ, —OC$_{2-6}$alkNRᵃRᵃ, —OC$_{2-6}$alkORᵃ, —SRᵃ, —S(=O)Rᵃ, —S(=O)₂Rᵃ, —S(=O)₂NRᵃRᵃ, —S(=O)₂N(Rᵃ)C(=O)Rᵃ, —S(=O)₂N(Rᵃ)C(=O)ORᵃ, —S(=O)₂N(Rᵃ)C(=O)NRᵃRᵃ, —NRᵃRᵃ, —N(Rᵃ)C(=O)Rᵃ, —N(Rᵃ)C(=O)ORᵃ, —N(Rᵃ)C(=O)NRᵃRᵃ, —N(Rᵃ)C(=NRᵃ)NRᵃRᵃ, —N(Rᵃ)S(=O)₂Rᵃ, —N(Rᵃ)S(=O)₂NRᵃRᵃ, —NRᵃC$_{2-6}$alkNRᵃRᵃ and —NRᵃC$_{2-6}$alkORᵃ;

R⁴ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk, C(=O)NH₂, C(=O)NHC$_{1-4}$alk, C(=O)N(C$_{1-4}$alk)C$_{1-4}$alk, N(H)C(=O)C$_{1-4}$alk, N(C$_{1-4}$alk)C(=O)C$_{1-4}$alk, $C_{1-4}$haloalk or an unsaturated 5-, 6- or 7-membered monocyclic ring containing 0, 1, 2, 3 or 4 atoms selected from N, O and S, but containing no more than one O or S, substituted by 0, 1, 2 or 3 substituents selected from halo, $C_{1-4}$alk, $C_{1-3}$haloalk, —OC$_{1-4}$alk, —NH₂, —NHC$_{1-4}$alk, —N(C$_{1-4}$alk)C$_{1-4}$alk;

R⁵ is, independently, in each instance, H, halo, nitro, cyano, $C_{1-4}$alk, OC$_{1-4}$alk, OC$_{1-4}$haloalk, NHC$_{1-4}$alk, N(C$_{1-4}$alk)C$_{1-4}$alk or $C_{1-4}$haloalk;

R⁶ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$; or $R^6$ is selected from H, halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)Ra, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$;

$R^7$ is H, $C_{1-6}$alk, —C(=O)N($R^a$)$R^a$, —C(=O)$R^b$ or $C_{1-4}$haloalk;

$R^a$ is independently, at each instance, H or $R^b$; and $R^b$ is independently, at each instance, phenyl, benzyl or $C_{1-6}$alk, the phenyl, benzyl and $C_{1-6}$alk being substituted by 0, 1, 2 or 3 substituents selected from halo, $C_{1-4}$alk, $C_{1-3}$haloalk, —O$C_{1-4}$alk, —NH$_2$, —NHC$_{1-4}$alk, —N($C_{1-4}$alk)$C_{1-4}$alk.

In another embodiment, in conjunction with any of the above or below embodiments,
$X^2$ is C($R^4$);
$X^3$ is C($R^5$);
$X^4$ is C($R^5$); and
$X^5$ is C($R^4$).

In another embodiment, in conjunction with any of the above or below embodiments,
$X^2$ is N;
$X^3$ is C($R^5$);
$X^4$ is C($R^5$); and
$X^5$ is C($R^4$).

In another embodiment, in conjunction with any of the above or below embodiments,
$X^2$ is C($R^4$);
$X^3$ is N;
$X^4$ is C($R^5$); and
$X^5$ is C($R^4$).

In another embodiment, in conjunction with any of the above or below embodiments,
$X^2$ is C($R^4$);
$X^3$ is C($R^5$);
$X^4$ is N; and
$X^5$ is C($R^4$).

In another embodiment, in conjunction with any of the above or below embodiments,
$X^2$ is C($R^4$);
$X^3$ is C($R^5$);
$X^4$ is C($R^5$); and
$X^5$ is N.

In another embodiment, in conjunction with any of the above or below embodiments, $R^1$ is selected from $C_{1-6}$alk and $C_{1-4}$haloalk.

In another embodiment, in conjunction with any of the above or below embodiments, $R^1$ is a direct-bonded unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups.

In another embodiment, in conjunction with any of the above or below embodiments, $R^1$ is a direct-bonded unsaturated 5-, 6- or 7-membered monocyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups.

In another embodiment, in conjunction with any of the above or below embodiments, $R^1$ is phenyl or pyridine, both of which are substituted by 0, 1, 2 or 3 substituents independently selected from halo, $C_{1-6}$alk and $C_{1-4}$haloalk.

In another embodiment, in conjunction with any of the above or below embodiments, $R^1$ is a methylene-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —OC$_{2-6}$alkN$R^aR^a$, —OC$_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups.

In another embodiment, in conjunction with any of the above or below embodiments, $R^1$ is an ethylene-linked saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$, wherein the available carbon atoms of the ring are additionally substituted by 0, 1 or 2 oxo or thioxo groups.

In another embodiment, in conjunction with any of the above or below embodiments, $R^2$ is selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any of the above or below embodiments, $R^2$ is selected from halo, $C_{1-6}$alk and $C_{1-4}$haloalk.

In another embodiment, in conjunction with any of the above or below embodiments, $R^2$ is H.

In another embodiment, in conjunction with any of the above or below embodiments, $R^1$ and $R^2$ together form a saturated or partially-saturated 2-, 3-, 4- or 5-carbon bridge substituted by 0, 1 or 2 substituents selected from halo, cyano, OH, O$C_{1-4}$alk, $C_{1-4}$alk, $C_{1-3}$haloalk, O$C_{1-4}$alk, NH$_2$, NH$C_{1-4}$alk and N($C_{1-4}$alk)$C_{1-4}$alk.

In another embodiment, in conjunction with any of the above or below embodiments, $R^3$ is selected from saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$ alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any of the above or below embodiments, $R^3$ is selected from saturated 5-, 6- or 7-membered monocyclic ring containing 1, 2, 3 or 4 atoms selected from N, O and S, but containing no more than one O or S, wherein the available carbon atoms of the ring are substituted by 0, 1 or 2 oxo or thioxo groups, wherein the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any of the above or below embodiments, $R^3$ is selected from saturated 5-, 6- or 7-membered monocyclic ring containing 1, 2, 3 or 4 atoms selected from N, O and S, but containing no more than one O or S, wherein the ring is substituted by 0, 1, 2 or 3 substituents independently selected from halo, $C_{1-6}$alk and $C_{1-4}$haloalk.

In another embodiment, in conjunction with any of the above or below embodiments, $R^3$ is selected from saturated 6-membered monocyclic ring containing 1 or 2 atoms selected from N, O and S, but containing no more than one O or S, wherein the ring is substituted by 0, 1, 2 or 3 substituents independently selected from halo, $C_{1-6}$alk and $C_{1-4}$haloalk.

In another embodiment, in conjunction with any of the above or below embodiments, $R^3$ is selected from saturated 6-membered monocyclic ring containing 1 or 2 atoms selected from N, O and S, but containing no more than one O or S.

In another embodiment, in conjunction with any of the above or below embodiments, $R^3$ is selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any of the above or below embodiments, $R^6$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 $R^2$ substituents, and the ring is additionally substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$ and —N$R^aC_{2-6}$alkO$R^a$.

In another embodiment, in conjunction with any of the above or below embodiments, $R^6$ is selected from saturated, partially-saturated or unsaturated 5-, 6- or 7-membered monocyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0, 1, 2 or 3 substituents independently selected from halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)

$R^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

In another embodiment, in conjunction with any of the above or below embodiments, $R^6$ is selected from saturated 5-, 6- or 7-membered monocyclic ring containing 1 or 2 atoms selected from N, O and S, but containing no more than one O or S, wherein the ring is substituted by 0, 1, 2 or 3 substituents independently selected from halo, C$_{1-6}$alk and C$_{1-4}$haloalk.

In another embodiment, in conjunction with any of the above or below embodiments, $R^6$ is selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$.

In another embodiment, in conjunction with any of the above or below embodiments, $R^6$ is cyano.

Another aspect of the invention relates to a method of treating PI3K-mediated conditions or disorders.

In certain embodiments, the PI3K-mediated condition or disorder is selected from rheumatoid arthritis, ankylosing spondylitis, osteoarthritis, psoriatic arthritis, psoriasis, inflammatory diseases, and autoimmune diseases. In other embodiments, the PI3K-mediated condition or disorder is selected from cardiovascular diseases, atherosclerosis, hypertension, deep venous thrombosis, stroke, myocardial infarction, unstable angina, thromboembolism, pulmonary embolism, thrombolytic diseases, acute arterial ischemia, peripheral thrombotic occlusions, and coronary artery disease. In still other embodiments, the PI3K-mediated condition or disorder is selected from cancer, colon cancer, glioblastoma, endometrial carcinoma, hepatocellular cancer, lung cancer, melanoma, renal cell carcinoma, thyroid carcinoma, cell lymphoma, lymphoproliferative disorders, small cell lung cancer, squamous cell lung carcinoma, glioma, breast cancer, prostate cancer, ovarian cancer, cervical cancer, and leukemia. In yet another embodiment, the PI3K-mediated condition or disorder is selected from type II diabetes. In still other embodiments, the PI3K-mediated condition or disorder is selected from respiratory diseases, bronchitis, asthma, and chronic obstructive pulmonary disease. In certain embodiments, the subject is a human.

Another aspect of the invention relates to the treatment of rheumatoid arthritis, ankylosing spondylitis, osteoarthritis, psoriatic arthritis, psoriasis, inflammatory diseases or autoimmune diseases comprising the step of administering a compound according to any of the above embodiments.

Another aspect of the invention relates to the treatment of rheumatoid arthritis, ankylosing spondylitis, osteoarthritis, psoriatic arthritis, psoriasis, inflammatory diseases and autoimmune diseases, inflammatory bowel disorders, inflammatory eye disorders, inflammatory or unstable bladder disorders, skin complaints with inflammatory components, chronic inflammatory conditions, autoimmune diseases, systemic lupus erythematosis (SLE), myestenia gravis, rheumatoid arthritis, acute disseminated encephalomyelitis, idiopathic thrombocytopenic purpura, multiples sclerosis, Sjoegren's syndrome and autoimmune hemolytic anemia, allergic conditions and hypersensitivity, comprising the step of administering a compound according to any of the above or below embodiments.

Another aspect of the invention relates to the treatment of cancers that are mediated, dependent on or associated with p110δ activity, comprising the step of administering a compound according to any of the above or below embodiments.

Another aspect of the invention relates to the treatment of cancers are selected from acute myeloid leukaemia, myelodysplastic syndrome, myelo-proliferative diseases, chronic myeloid leukaemia, T-cell acute lymphoblastic leukaemia, B-cell acute lymphoblastic leukaemia, non-hodgkins lymphoma, B-cell lymphoma, solid tumors and breast cancer, comprising the step of administering a compound according to any of the above or below embodiments.

Another aspect of the invention relates to a pharmaceutical composition comprising a compound according to any of the above embodiments and a pharmaceutically-acceptable diluent or carrier.

Another aspect of the invention relates to the use of a compound according to any of the above embodiments as a medicament.

Another aspect of the invention relates to the use of a compound according to any of the above embodiments in the manufacture of a medicament for the treatment of rheumatoid arthritis, ankylosing spondylitis, osteoarthritis, psoriatic arthritis, psoriasis, inflammatory diseases, and autoimmune diseases.

The compounds of this invention may have in general several asymmetric centers and are typically depicted in the form of racemic mixtures. This invention is intended to encompass racemic mixtures, partially racemic mixtures and separate enantiomers and diastereomers.

Unless otherwise specified, the following definitions apply to terms found in the specification and claims:

"C$_{\alpha-\beta}$alk" means an alkyl group comprising a minimum of α and a maximum of β carbon atoms in a branched, cyclical or linear relationship or any combination of the three, wherein α and β represent integers. The alkyl groups described in this section may also contain one or two double or triple bonds. Examples of C$_{1-6}$alk include, but are not limited to the following:

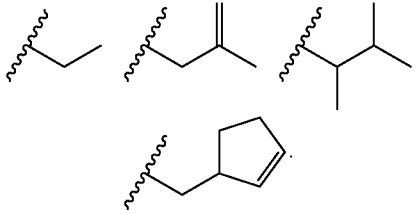

"Benzo group", alone or in combination, means the divalent radical C$_4$H$_4$=, one representation of which is —CH=CH—CH=CH—, that when vicinally attached to another ring forms a benzene-like ring—for example tetrahydronaphthylene, indole and the like.

The terms "oxo" and "thioxo" represent the groups =O (as in carbonyl) and =S (as in thiocarbonyl), respectively.

"Halo" or "halogen" means a halogen atoms selected from F, Cl, Br and I. "C$_{V-W}$haloalk" means an alk group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

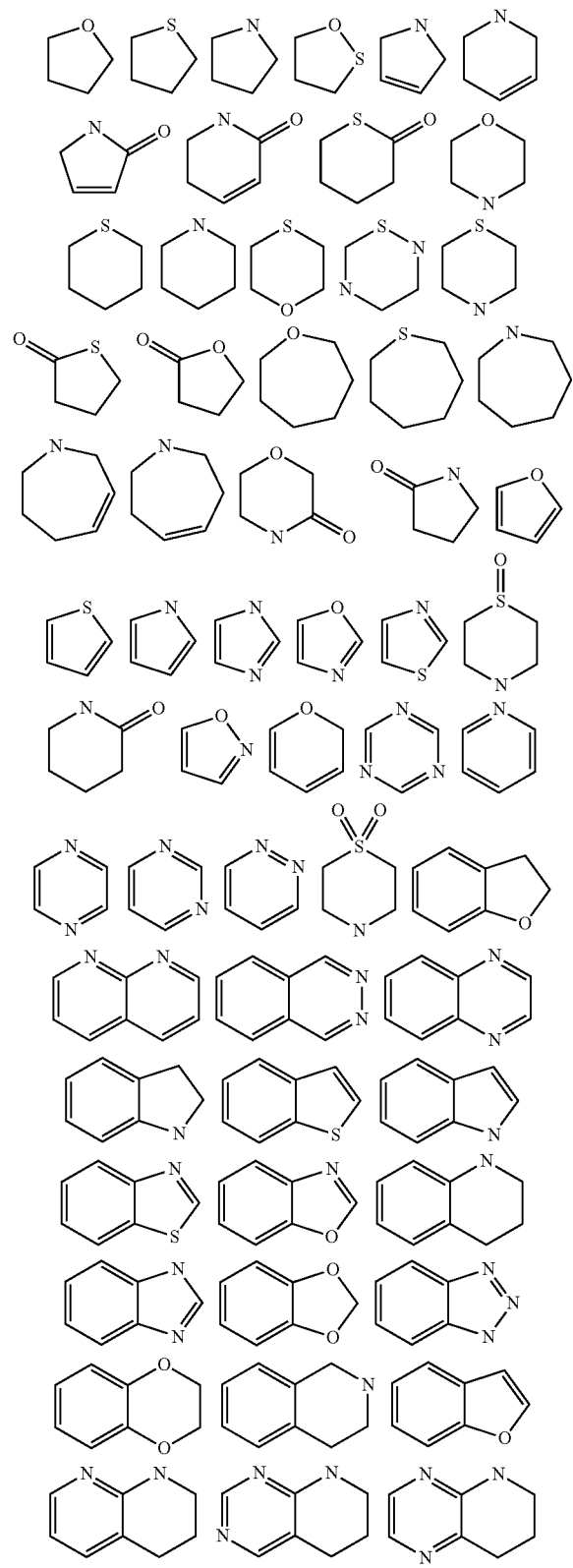

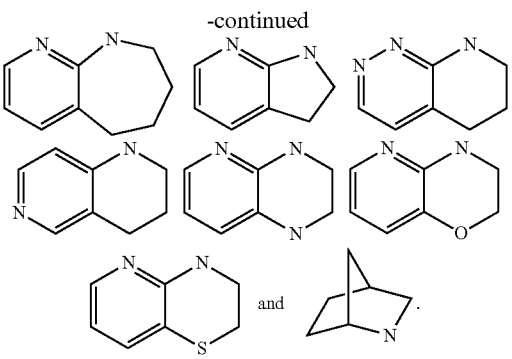

"Available nitrogen atoms" are those nitrogen atoms that are part of a heterocycle and are joined by two single bonds (e.g. piperidine), leaving an external bond available for substitution by, for example, H or $CH_3$.

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al., J. Pharm. Sci. 66:1 (1977).

"Saturated, partially saturated or unsaturated" includes substituents saturated with hydrogens, substituents completely unsaturated with hydrogens and substituents partially saturated with hydrogens.

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6-10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, trifluoroacetyl, trichloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl. Silyl protecting groups are silicon atoms optionally substituted by one or more alkyl, aryl and aralkyl groups. Suitable silyl protecting groups include, but are not limited to, trimethylsilyl, triethylsilyl, triisopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-trisilyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

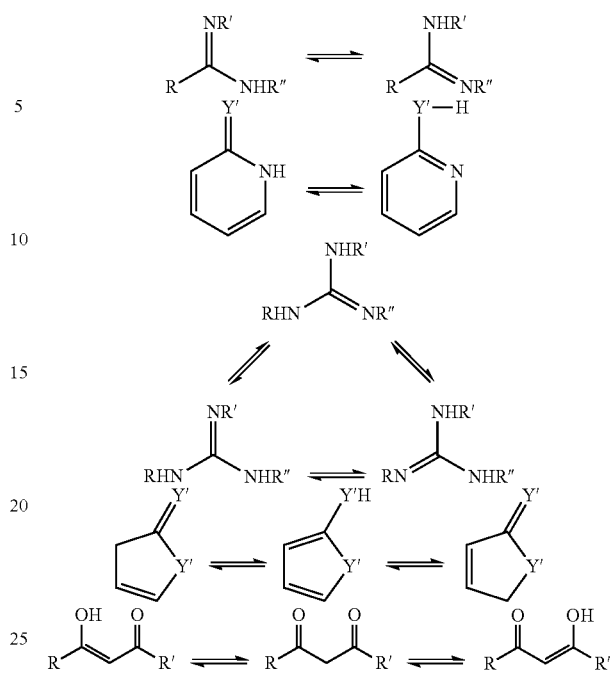

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

EXPERIMENTAL

The following abbreviations are used:
aq.—aqueous
BINAP—2,2'-bis(diphenylphosphino)-1,1'-binaphthyl
concd—concentrated
DCM—dichloromethane
DMF—N,N-dimethylformamide
DMSO—dimethylsulfoxide
Et$_2$O—diethyl ether
EtOAc—ethyl acetate
EtOH—ethyl alcohol
h—hour(s)
min—minutes
MeOH—methyl alcohol
NMP—1-methyl-2-pyrrolidinone
rt—room temperature
satd—saturated
TFA—trifluoroacetic acid
THF—tetrahydrofuran
X-Phos—2-dicyclohexylphosphino-2',4',6'-tri-isopropyl-1,1'-biphenyl General Reagents and solvents used below can be obtained from commercial sources. $^1$H-NMR spectra were recorded on a Bruker 400 MHz and 500 MHz NMR spectrometer. Significant peaks are tabulated in the order: number of protons, multiplicity (s, singlet; d, doublet; t, triplet; q, quartet; m, multiplet; br s, broad singlet), and coupling constant(s) in Hertz (Hz). Mass spectrometry results are reported as the ratio of mass over charge, followed by the relative abundance of each ion (in parentheses Electrospray ionization (ESI) mass spectrometry analysis was conducted on a Agilent 1100 series LC/MSD electrospray mass spectrometer.

All compounds could be analyzed in the positive ESI mode using acetonitrile:water with 0.1% formic acid as the delivery solvent. Reverse phase analytical HPLC was carried out using a Agilent 1200 series on Agilent Eclipse XDB-C18 5 μm column (4.6×150 mm) as the stationary phase and eluting with acetonitrile:H$_2$O with 0.1% TFA. Reverse phase semi-prep HPLC was carried out using a Agilent 1100 Series on a Phenomenex Gemini™ 10 μm C18 column (250×21.20 mm) as the stationary phase and eluting with acetonitrile:H$_2$O with 0.1% TFA.

Procedure A

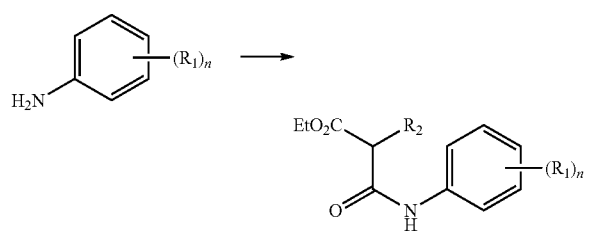

A mixture of the substituted aniline (1 equiv.) in pyridine (2 equiv.) was treated with diethyl alkylmalonate (1.5 equiv.) and the stirred mixture was heated at 130° C. for 24 h. After this time the reaction was treated with diethyl alkylmalonate (0.5 equiv.) and heated at 130° C. for an additional 12 h. After this time the reaction was cooled to rt and evaporated under reduced pressure. The crude product was taken up in DCM, washed with satd aq. bicarbonate and the separated organic layer was dried over magnesium sulfate, filtered and evaporated under reduced pressure. The crude product was dissolved in benzene and evaporated under reduced pressure. The crude product was purified by column chromatography on silica (using a gradient of hexanes:EtOAc, 1:0 to 3:1 as eluant) to provide ethyl substituted phenylamino-oxopropanoates.

Procedure B

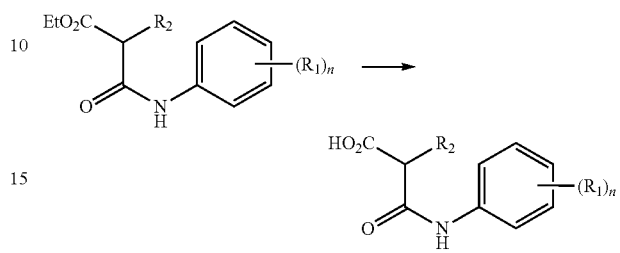

A mixture of the ethyl substituted phenylamino-oxopropanoate (1 equiv.) in THF-water (4:1, 0.878M) was treated with sodium hydroxide (1.2 equiv.) and stirred at rt for 1 h. After this time the reaction was acidified to pH 2 with concd HCl and then it was extracted with EtOAc. The separated organic layer was dried over magnesium sulfate, filtered and evaporated under reduced pressure to give substituted phenylamino-oxopropanoic acids.

Procedure C

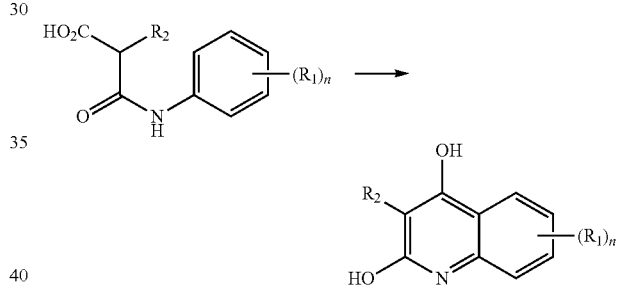

A mixture of phenylamino-oxopropanoic acid in polyphosphoric acid (0.6M) was stirred at 130° C. for 2 h. After this time the reaction was cooled to rt and treated with 2M aq. sodium hydroxide until a precipitate formed. The precipitate was filtered and washed with 1M aq. sodium hydroxide and dried under vacuum to give substituted quinoline diols.

Procedure D

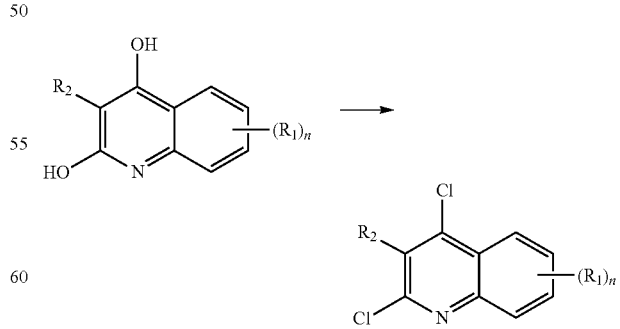

A mixture of the quinoline diol (1 equiv.) and phosphorus oxychloride (10 equiv.) was heated at 100° C. for 2 h. After this time the reaction was cooled to rt and evaporated under reduced pressure. The resulting brown residue was taken up in DCM and washed with water. The separated organic layer was dried over magnesium sulfate, filtered and evaporated under reduced pressure. The product was then purified by column chromatography (using a 9 to 1 mixture of hexanes and EtOAc as eluant) to give the substituted dichloroquinolines.

Procedure E

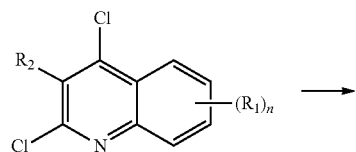

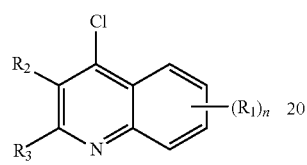

A mixture of the substituted dichloroquinoline (1 equiv.), the Stille reagent (1 equiv.) and tetrakis(triphenylphosphine)palladium (0.1 equiv.) in toluene (0.21M) was heated at reflux overnight. After this time the reaction was cooled to rt and treated with EtOAc and water. The separated organic layer was dried over magnesium sulfate, filtered and evaporated in vacuo. Column chromatography gave the substituted 4-chloro quinolines.

Procedure F

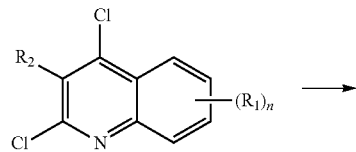

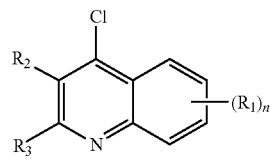

A mixture of the substituted dichloroquinoline (1 equiv.), the boronic acid (1 equiv.), sodium carbonate (2 equiv.) and tetrakis(triphenylphosphine)palladium (0.1 equiv.) in toluene-water (5:2, 0.15M) was heated at reflux overnight. After this time the reaction was cooled to rt and treated with EtOAc and water. The separated organic layer was dried over magnesium sulfate, filtered and evaporated in vacuo. Column chromatography gave the substituted 4-chloro quinolines.

Procedure G

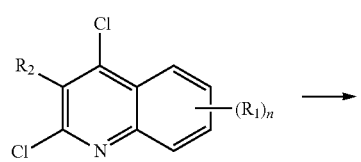

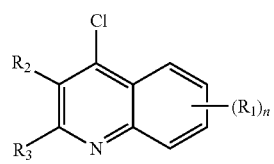

A mixture of the substituted dichloroquinoline (1 equiv.) and the amine ($R_3$—H, 1 equiv.) in isopropanol (0.4M) was heated in a sealed tube overnight at 85° C. The reaction was cooled to rt and concd to dryness under reduced pressure. The residue was then purified by medium pressure chromatography to give the corresponding substituted 4-chloroquinolines.

Procedure H

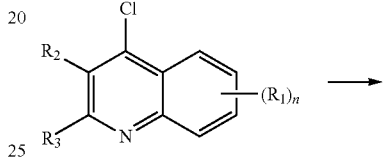

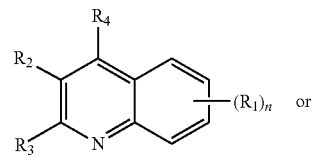

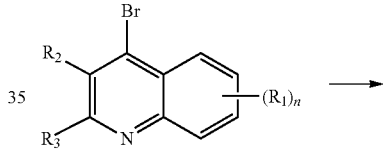

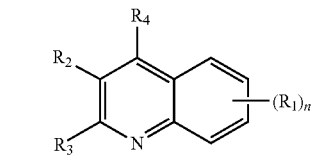

A mixture of the substituted 4-chloroquinoline or 4-bromoquinoline (1 equiv.) and the amine ($R_4$—H, 1.1 equiv.), sodium tert-butoxide (2.5 equiv.), X-Phos (0.16 equiv.) and tris(dibenzylideneacetone)dipalladium(0) (0.04 equiv.) in a suitable solvent (0.5M) was heated in an oil bath or a microwave reactor at 110° C. for 45 min. The reaction was cooled to rt and diluted with water. The mixture was extracted with EtOAc, DCM or a 10% MeOH:DCM mixture. The combined organic layers were dried over magnesium sulfate and filtered. The filtrate was concd under reduced pressure and the residue was then purified by medium pressure chromatography to give the corresponding substituted quinolines.

Procedure I

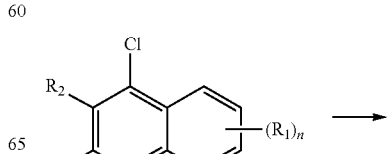

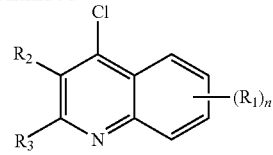

or

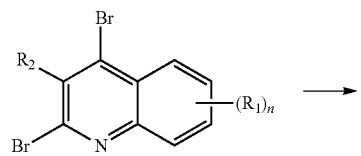

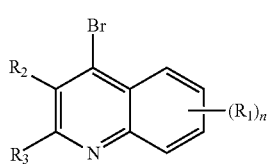

A mixture of the substituted 4-chloroquinoline or 4-bromoquinoline (1 equiv.), the other nitrogen containing reagent (R$_3$—H, 1.1 equiv.), potassium carbonate (2.5 equiv.), di-tert-butyl(2',4',6'-triisopropyl-3,4,5,6-tetramethylbiphenyl-2-yl)phosphine (0.05 equiv.), activated three angstrom molecular sieves and tris(dibenzyl-ideneacetone)dipalladium(0) (0.02 equiv.) in a suitable solvent (0.5M) was heated in an oil bath or a microwave reactor at 110° C. for 3 h. The reaction was cooled to rt and filtered. To the filtrate was added water and the mixture was extracted with EtOAc, DCM or a 10% MeOH:DCM mixture. The combined organic layers were dried over magnesium sulfate and filtered. The filtrate was concd under reduced pressure and the residue was then purified by medium pressure chromatography to give the corresponding substituted quinolines.

Procedure J

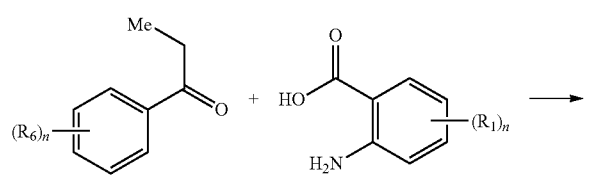

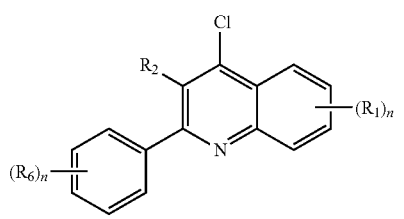

A mixture of the aminobenzoic acid (1.3 equiv.) and the aryl propanone (1.0 equiv.) in phosphorous oxychloride (0.5M) was heated to 90° C. for 2 h then concd under reduced pressure. The concentrate was partitioned between DCM and satd aq. sodium bicarbonate solution, stirring vigorously for 1 h. The organic extract was washed with water then brine, stirred over anhydrous magnesium sulfate, filtered and the filtrate concd under reduced pressure. The product was isolated by column chromatography on silica gel, eluting with EtOAc gradient in hexane.

Procedure K

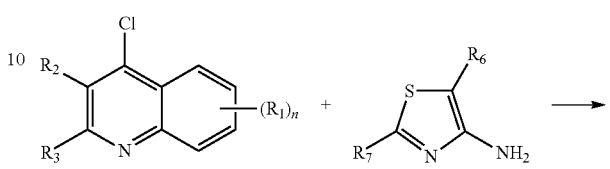

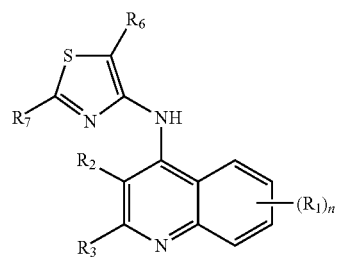

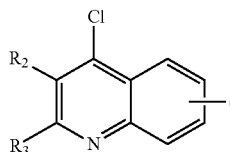 + 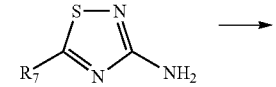

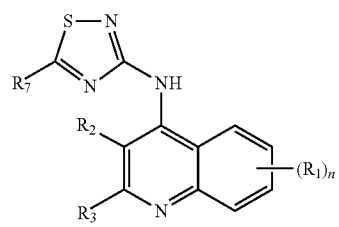

Method 1:

A mixture of the substituted quinoline (1.0 equiv.), the substituted aniline (1.0 equiv.) and 4.0 N hydrochloric acid solution in 1,4-dioxane (1.0 equiv.) in MeOH (0.4M) was heated in a microwave at 150° C. for 2 h. The reaction was partitioned between DCM and satd aq. sodium bicarbonate solution. The organic separation was stirred over anhydrous magnesium sulfate, filtered and the filtrate concd under reduced pressure to afford product, which was isolated by column chromatography on silica gel.

Method 2:

A mixture of the substituted quinoline (2.0 equiv.), the substituted aniline (1.0 equiv.) and 4 N hydrochloric acid in 1,4-dioxane (0.1 equiv.) in 1-methyl-2-pyrrolidinone (0.8M) was heated in a microwave at 150° C. for 4 h. The reaction was partitioned between EtOAc and satd aq. sodium bicarbonate. The organic separation was washed with water then brine, stirred over anhydrous magnesium sulfate, filtered and the

Example 1

Preparation of N-(7-fluoro-3-methyl-2-(pyridin-2-yl)quinolin-4-yl)-5-morpholino-1,2,4-thiadiazol-3-amine 7-Fluoro-N-(4-methoxybenzyl)-3-methyl-2-(pyridin-2-yl)quinolin-4-amine

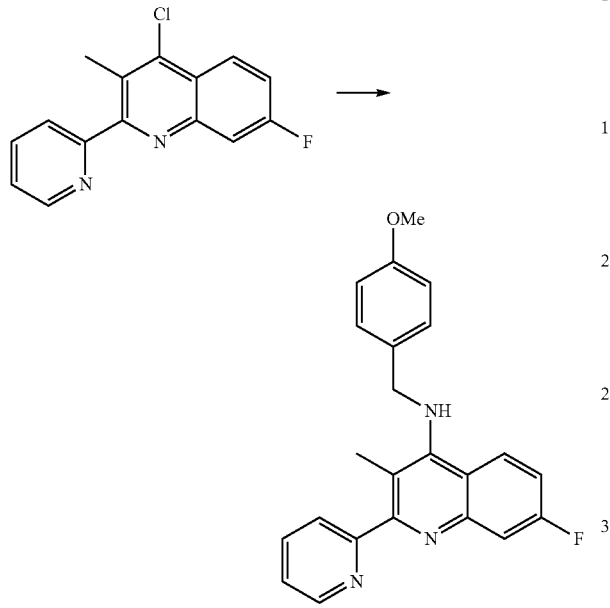

To a stirred solution of 2-(dicyclohexylphosphino)-2',4',6'-triisopropylbiphenyl (175 mg, 0.37 mmol), tris(dibenzylideneacetone)dipalladium(0) (168 mg, 0.183 mmol), 4-chloro-7-fluoro-3-methyl-2-(pyridin-2-yl)quinoline (0.50 g, 1.83 mmol) and 4-methoxybenzylamine (238 μL, 1.83 mmol) in toluene (6112 μL, 1.83 mmol) was added sodium tert-butoxide (352 mg, 3.67 mmol). The reaction mixture was heated to 100° C. and stirred for 0.5 hours. After which, the crude reaction mixture was filtered through a plug of alumina eluting with ethyl acetate, the filtrate was concentrated in vacuo. The crude product was purified by column chromatography on alumina (0 to 50% ethyl acetate in hexanes) to give the desired product 7-fluoro-N-(4-methoxybenzyl)-3-methyl-2-(pyridin-2-yl)quinolin-4-amine. Mass Spectrum (ESI) m/e=374.1 (M+1).

7-Fluoro-3-methyl-2-(pyridin-2-yl)quinolin-4-amine

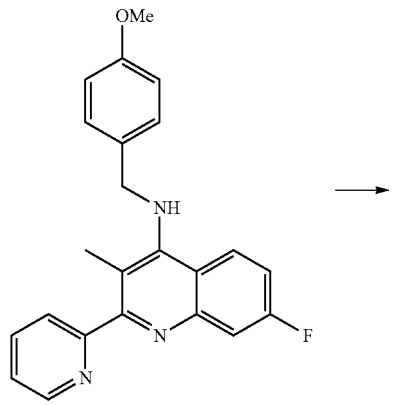

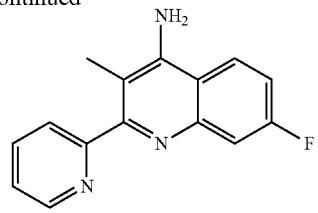

To a stirred solution of 7-fluoro-N-(4-methoxybenzyl)-3-methyl-2-(pyridin-2-yl)quinolin-4-amine (0.486 g, 1.30 mmol) in dichloromethane (13.0 mL) was added TFA (0.5 mL, 6.49 mmol). Stirring continued at 23° C. for 26 hours. After which, the reaction was concentrated in vacuo, dissolved in ethyl acetate and washed with a saturated solution of sodium bicarbonate. The combined organic layers were concentrated in vacuo and purified on silica gel eluting with 0-10% methanol in dichloromethane to give the desired product 7-fluoro-3-methyl-2-(pyridin-2-yl)quinolin-4-amine. Mass Spectrum (ESI) m/e=254.1 (M+1).

N-(7-Fluoro-3-methyl-2-(pyridin-2-yl)quinolin-4-yl)-5-morpholino-1,2,4-thiadiazol-3-amine

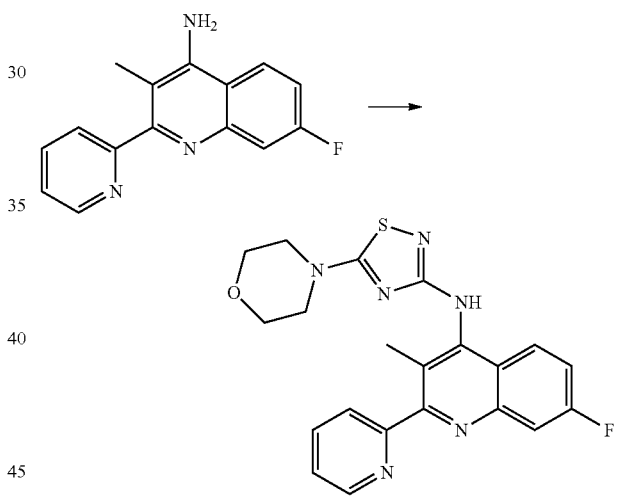

To a stirred solution of dicyclohexyl(2',4',6'-triisopropylbiphenyl-2-yl)phosphine (0.018 g, 0.038 mmol), 4-(3-bromo-1,2,4-thiadiazol-5-yl)morpholine (0.059 g, 0.24 mmol), 7-fluoro-3-methyl-2-(pyridin-2-yl)quinolin-4-amine (0.06 g, 0.24 mmol) and $Pd_2\,dba_3$ (0.009 g, 9.48 μmol) in toluene (2.4 mL) was added sodium tert-butoxide (0.057 g, 0.592 mmol). The reaction mixture was heated to 100° C. and stirred for 1 hour. The crude reaction mixture was filtered through a plug of alumina eluting with (dichloromethane/methanol; 3/1), the filtrate was concentrated in vacuo. The crude product was purified by column chromatography on alumina (0-60% ethyl acetate/hexanes) to give the desired product. The desired product was further purified with HPLC (10-90% of 0.1% TFA acetonitrile solution in 0.1% TFA water solution.) The desired fractions were concentrated then diluted with ethyl acetate. After washing twice with saturated aq. sodium bicarbonate solution, the solvent was removed under reduced pressure to yield pure product N-(7-fluoro-3-methyl-2-(pyridin-2-yl)quinolin-4-yl)-5-morpholino-1,2,4-thiadiazol-3-amine. $^1H$ NMR (400 MHz, $CD_2Cl_2$) δ ppm 8.65 (1H, d, J=3.9 Hz), 8.03 (1H, dd, J=9.2, 5.9 Hz), 7.94 (1H, td, J=7.7, 1.8 Hz), 7.74 (1H, d, J=7.8 Hz), 7.67 (1H, dd, J=10.0, 2.7 Hz), 7.39-7.49 (1H, m), 7.32 (1H, ddd, J=9.3, 8.2, 2.4 Hz), 3.71-3.83 (4H, m), 3.37-3.50 (4H, m), 2.28 (3H, s). Mass Spectrum (ESI) m/e=423.2 (M+1).

Biological Assays

Recombinant Expression of PI3Ks

Full length p110 subunits of PI3k α, β and δ, N-terminally labeled with polyHis tag, were coexpressed with p85 with Baculo virus expression vectors in sf9 insect cells. P110/p85 heterodimers were purified by sequential Ni-NTA, Q-HP, Superdex-100 chromatography. Purified α, β and δ isozymes were stored at −20° C. in 20 mM Tris, pH 8, 0.2M NaCl, 50% glycerol, 5 mM DTT, 2 mM Na cholate. Truncated PI3Kγ, residues 114-1102, N-terminally labeled with polyHis tag, was expessed with Baculo virus in Hi5 insect cells. The γ isozyme was purified by sequential Ni-NTA, Superdex-200, Q-HP chromatography. The γ isozyme was stored frozen at −80° C. in $NaH_2PO_4$, pH 8, 0.2M NaCl, 1% ethylene glycol, 2 mM β-mercaptoethanol.

|  | Alpha | Beta | Delta | gamma |
| --- | --- | --- | --- | --- |
| 50 mM Tris | pH 8 | pH 7.5 | pH 7.5 | pH 8 |
| MgCl2 | 15 mM | 10 mM | 10 mM | 15 mM |
| Na cholate | 2 mM | 1 mM | 0.5 mM | 2 mM |
| DTT | 2 mM | 1 mM | 1 mM | 2 mM |
| ATP | 1 uM | 0.5 uM | 0.5 uM | 1 uM |
| PIP2 | none | 2.5 uM | 2.5 uM | none |
| time | 1 h | 2 h | 2 h | 1 h |
| [Enzyme] | 15 nM | 40 nM | 15 nM | 50 nM |

In Vitro PI3K Enzyme Assays

A PI3K Alphascreen® assay (PerkinElmer, Waltham, Mass.) was used to measure the activity of a panel of four phosphoinositide 3-kinases: PI3Kα, PI3Kβ, PI3Kγ, and PI3Kδ. Enzyme reaction buffer was prepared using sterile water (Baxter, Deerfield, Ill.) and 50 mM Tris HCl pH 7, 14 mM $MgCl_2$, 2 mM sodium cholate, and 100 mM NaCl. 2 mM DTT was added fresh the day of the experiment. The Alphascreen buffer was made using sterile water and 10 mM Tris HCl pH 7.5, 150 mM NaCl, 0.10% Tween 20, and 30 mM EDTA. 1 mM DTT was added fresh the day of the experiment. Compound source plates used for this assay were 384-well Greiner clear polypropylene plates containing test compounds at 5 mM and diluted 1:2 over 22 concentrations. Columns 23 and 24 contained only DMSO as these wells comprised the positive and negative controls, respectively. Source plates were replicated by transferring 0.5 uL per well into 384-well Optiplates (PerkinElmer, Waltham, Mass.).

Each PI3K isoform was diluted in enzyme reaction buffer to 2× working stocks. PI3Kα was diluted to 1.6 nM, PI3Kβ was diluted to 0.8 nM, PI3Kγ was diluted to 15 nM, and PI3Kδ was diluted to 1.6 nM. P1(4,5)P2 (Echelon Biosciences, Salt Lake City, Utah) was diluted to 10 μM and ATP was diluted to 20 μM. This 2× stock was used in the assays for PI3Kα and PI3Kβ. For assay of PI3Kγ and PI3Kδ, PI(4,5)P2 was diluted to 10 μM and ATP was diluted to 8 μM to prepare a similar 2× working stock. Alphascreen reaction solutions were made using beads from the anti-GST Alphascreen kit (PerkinElmer, Waltham, Mass.). Two 4× working stocks of the Alphascreen reagents were made in Alphascreen reaction buffer. In one stock, biotinylated-$IP_4$ (Echelon Biosciences, Salt Lake City, Utah) was diluted to 40 nM and streptavadin-donor beads were diluted to 80 μg/mL. In the second stock, $PIP_3$-binding protein (Echelon Biosciences, Salt Lake City, Utah) was diluted to 40 nM and anti-GST-acceptor beads were diluted to 80 μg/mL. As a negative control, a reference inhibitor at a concentration >>Ki (40 uM) was included in column 24 as a negative (100% inhibition) control.

Using a 384-well Multidrop (Titertek, Huntsville, Ala.), 10 μL/well of 2× enzyme stock was added to columns 1-24 of the assay plates for each isoform. 10 μL/well of the appropriate substrate 2× stock (containing 20 μM ATP for the PI3Kα and β assays and containing 8 μM ATP for the PI3Kγ and δ assays) was then added to Columns 1-24 of all plates. Plates were then incubated at room temperature for 20 minutes. In the dark, 10 μL/well of the donor bead solution was added to columns 1-24 of the plates to quench the enzyme reaction. The plates were incubated at room temperature for 30 minutes. Still in the dark, 10 μL/well of the acceptor bead solution was added to columns 1-24 of the plates. The plates were then incubated in the dark for 1.5 hours. The plates were read on an Envision multimode Plate Reader (PerkinElmer, Waltham, Mass.) using a 680 nm excitation filter and a 520-620 nm emission filter.

Alternative In Vitro Enzyme Assays.

Assays were performed in 25 μL with the above final concentrations of components in white polyproplyene plates (Costar 3355). Phospatidyl inositol phosphoacceptor, PtdIns(4,5)P2 P4508, was from Echelon Biosciences. The ATPase activity of the alpha and gamma isozymes was not greatly stimulated by PtdIns(4,5)P2 under these conditions and was therefore omitted from the assay of these isozymes. Test compounds were dissolved in dimethyl sulfoxide and diluted with three-fold serial dilutions. The compound in DMSO (1 μL) was added per test well, and the inhibition relative to reactions containing no compound, with and without enzyme was determined. After assay incubation at rt, the reaction was stopped and residual ATP determined by addition of an equal volume of a commercial ATP bioluminescence kit (Perkin Elmer EasyLite) according to the manufacturer's instructions, and detected using a AnalystGT luminometer.

Human B Cells Proliferation Stimulate by Anti-IgM

Isolate Human B Cells:

Isolate PBMCs from Leukopac or from human fresh blood. Isolate human B cells by using Miltenyi protocol and B cell isolation kit II.—human B cells were Purified by using AutoMacs™ column.

Activation of Human B Cells

Use 96 well Flat bottom plate, plate 50000/well purified B cells in B cell proliferation medium (DMEM+5% FCS, 10 mM Hepes, 50 μM 2-mercaptoethanol); 150 μL medium contain 250 ng/mL CD40L LZ recombinant protein (Amgen) and 2 μg/mL anti-Human IgM antibody (Jackson ImmunoReseach Lab.#109-006-129), mixed with 50 μL B cell medium containing PI3K inhibitors and incubate 72 h at 37° C. incubator. After 72 h, pulse labeling B cells with 0.5-1 uCi/well $^3$H thymidine for overnight ~18 h, and harvest cell using TOM harvester.

Human B Cells Proliferation Stimulate by IL-4

Isolate Human B Cells:

Isolate human PBMCs from Leukopac or from human fresh blood. Isolate human B cells using Miltenyi protocol—B cell isolation kit. Human B cells were purified by AutoMacs.column.

Activation of Human B Cells

Use 96-well flat bottom plate, plate 50000/well purified B cells in B cell proliferation medium (DMEM+5% FCS, 50 μM 2-mercaptoethanol, 10 mM Hepes). The medium (150 μL) contain 250 ng/mL CD40L LZ recombinant protein (Amgen) and 10 ng/mL IL-4 (R&D system #204-IL-025), mixed with 50 150 μL B cell medium containing compounds and incubate 72 h at 37° C. incubator. After 72 h, pulse labeling B cells with 0.5-1 uCi/well 3H thymidine for overnight ~18 h, and harvest cell using TOM harvester.

Specific T Antigen (Tetanus Toxoid) Induced Human PBMC Proliferation Assays

Human PBMC are prepared from frozen stocks or they are purified from fresh human blood using a Ficoll gradient. Use 96 well round-bottom plate and plate $2\times10^5$ PBMC/well with culture medium (RPMI1640+10% FCS, 50 uM 2-Mercaptoethanol, 10 mM Hepes). For $IC_{50}$ determinations, PI3K inhibitors was tested from 10 μM to 0.001 μM, in half log increments and in triplicate. Tetanus toxoid, T cell specific antigen (University of Massachusetts Lab) was added at 1 μg/mL and incubated 6 days at 37° C. incubator. Supernatants are collected after 6 days for IL2 ELISA assay, then cells are pulsed with $^3$H-thymidine for ~18 h to measure proliferation.

GFP Assays for Detecting Inhibition of Class Ia and Class III PI3K

AKT1 (PKBa) is regulated by Class Ia PI3K activated by mitogenic factors (IGF-1, PDGF, insulin, thrombin, NGF, etc.). In response to mitogenic stimuli, AKT1 translocates from the cytosol to the plasma membrane Forkhead (FKHRL1) is a substrate for AKT1. It is cytoplasmic when phosphorylated by AKT (survival/growth). Inhibition of AKT (stasis/apoptosis)-forkhead translocation to the nucleus FYVE domains bind to PI(3)P. the majority is generated by constitutive action of PI3K Class III AKT Membrane Ruffling Assay (CHO-1R-AKT1-EGFP Cells/GE Healthcare)

Wash cells with assay buffer. Treat with compounds in assay buffer 1 h. Add 10 ng/mL insulin. Fix after 10 min at room temp and image Forkhead Translocation Assay (MDA MB468 Forkhead-DiversaGFP Cells)

Treat cells with compound in growth medium 1 h. Fix and image.

Class III PI(3)P assay (U2OS EGFP-2×FYVE Cells/GE Healthcare)

Wash cells with assay buffer. Treat with compounds in assay buffer 1 h. Fix and image.

Control for all 3 assays is 10 uM Wortmannin:

AKT is cytoplasmic

Forkhead is nuclear

PI(3)P depleted from endosomes

Biomarker Assay: B-Cell Receptor Stimulation of CD69 or B7.2 (CD86) Expression

Heparinized human whole blood was stimulated with 10 μg/mL anti-IgD (Southern Biotech, #9030-01). 90 μL of the stimulated blood was then aliquoted per well of a 96-well plate and treated with 10 μL of various concentrations of blocking compound (from 10-0.0003 μM) diluted in IMDM+ 10% FBS (Gibco). Samples were incubated together for 4 h (for CD69 expression) to 6 h (for B7.2 expression) at 37° C. Treated blood (50 μL) was transferred to a 96-well, deep well plate (Nunc) for antibody staining with 10 μL each of CD45-PerCP (BD Biosciences, #347464), CD19-FITC (BD Biosciences, #340719), and CD69-PE (BD Biosciences, #341652). The second 50 μL of the treated blood was transferred to a second 96-well, deep well plate for antibody staining with 10 μL each of CD19-FITC (BD Biosciences, #340719) and CD86-PeCy5 (BD Biosciences, #555666). All stains were performed for 15-30 min in the dark at rt. The blood was then lysed and fixed using 450 μL of FACS lysing solution (BD Biosciences, #349202) for 15 min at rt. Samples were then washed 2× in PBS+2% FBS before FACS analysis. Samples were gated on either CD45/CD19 double positive cells for CD69 staining, or CD19 positive cells for CD86 staining Gamma Counterscreen: Stimulation of Human Monocytes for Phospho-AKT Expression A human monocyte cell line, THP-1, was maintained in RPMI+10% FBS (Gibco). One day before stimulation, cells were counted using trypan blue exclusion on a hemocytometer and suspended at a concentration of $1\times10^6$ cells per mL of media. 100 μL of cells plus media ($1\times10^5$ cells) was then aliquoted per well of 4-96-well, deep well dishes (Nunc) to test eight different compounds. Cells were rested overnight before treatment with various concentrations (from 10-0.0003 μM) of blocking compound. The compound diluted in media (12 μL) was added to the cells for 10 min at 37° C. Human MCP-1 (12 μL, R&D Diagnostics, #279-MC) was diluted in media and added to each well at a final concentration of 50 ng/mL. Stimulation lasted for 2 min at rt. Pre-warmed FACS Phosflow Lyse/Fix buffer (1 mL of 37° C.) (BD Biosciences, #558049) was added to each well. Plates were then incubated at 37° C. for an additional 10-15 min. Plates were spun at 1500 rpm for 10 min, supernatant was aspirated off, and 1 mL of ice cold 90% MeOH was added to each well with vigorous shaking Plates were then incubated either overnight at −70° C. or on ice for 30 min before antibody staining Plates were spun and washed 2× in PBS+2% FBS (Gibco). Wash was aspirated and cells were suspended in remaining buffer. Rabbit pAKT (50 μL, Cell Signaling, #4058L) at 1:100, was added to each sample for 1 h at rt with shaking Cells were washed and spun at 1500 rpm for 10 min. Supernatant was aspirated and cells were suspended in remaining buffer. Secondary antibody, goat anti-rabbit Alexa 647 (50 μL, Invitrogen, #A21245) at 1:500, was added for 30 min at rt with shaking Cells were then washed 1× in buffer and suspended in 150 μL of buffer for FACS analysis. Cells need to be dispersed very well by pipetting before running on flow cytometer. Cells were run on an LSR II (Becton Dickinson) and gated on forward and side scatter to determine expression levels of pAKT in the monocyte population.

Gamma Counterscreen Stimulation of Monocytes for Phospho-AKT Expression in Mouse Bone Marrow Mouse femurs were dissected from five female BALB/c mice (Charles River Labs.) and collected into RPMI+10% FBS media (Gibco). Mouse bone marrow was removed by cutting the ends of the femur and by flushing with 1 mL of media using a 25 gauge needle. Bone marrow was then dispersed in media using a 21 gauge needle. Media volume was increased to 20 mL and cells were counted using trypan blue exclusion on a hemocytometer. The cell suspension was then increased to $7.5\times10^6$ cells per 1 mL of media and 100 μL ($7.5\times10^5$ cells) was aliquoted per well into 4-96-well, deep well dishes (Nunc) to test eight different compounds. Cells were rested at 37° C. for 2 h before treatment with various concentrations (from 10-0.0003 μM) of blocking compound. Compound diluted in media (12 μL) was added to bone marrow cells for 10 min at 37° C. Mouse MCP-1 (12 μL, R&D Diagnostics, #479-JE) was diluted in media and added to each well at a final concentration of 50 ng/mL. Stimulation lasted for 2 min at rt. 1 mL of 37° C. pre-warmed FACS Phosflow Lyse/Fix buffer (BD Biosciences, #558049) was added to each well. Plates were then incubated at 37° C. for an additional 10-15 min. Plates were spun at 1500 rpm for 10 min. Supernatant was aspirated off and 1 mL of ice cold 90% MeOH was added to each well with vigorous shaking Plates were then incubated either overnight at −70° C. or on ice for 30 min before antibody staining Plates were spun and washed 2× in PBS+ 2% FBS (Gibco). Wash was aspirated and cells were suspended in remaining buffer. Fc block (2 μL, BD Pharmingen, #553140) was then added per well for 10 min at rt. After block, 50 μL of primary antibodies diluted in buffer; CD11b-Alexa488 (BD Biosciences, #557672) at 1:50, CD64-PE (BD Biosciences, #558455) at 1:50, and rabbit pAKT (Cell Signaling, #4058L) at 1:100, were added to each sample for 1 h at rt with shaking Wash buffer was added to cells and spun at 1500 rpm for 10 min. Supernatant was aspirated and cells were suspended in remaining buffer. Secondary antibody; goat anti-rabbit Alexa 647 (50 μL, Invitrogen, #A21245) at 1:500, was added for 30 min at rt with shaking Cells were then washed 1× in buffer and suspended in 100 μL of buffer for FACS analysis. Cells were run on an LSR II (Becton Dickinson) and gated on CD11b/CD64 double positive cells to determine expression levels of pAKT in the monocyte population.

pAKT In Vivo Assay

Vehicle and compounds are administered p.o. (0.2 mL) by gavage (Oral Gavage Needles Popper & Sons, New Hyde Park, N.Y.) to mice (Transgenic Line 3751, female, 10-12 wks Amgen Inc, Thousand Oaks, Calif.) 15 min prior to the injection i.v (0.2 mLs) of anti-IgM FITC (50 ug/mouse) (Jackson Immuno Research, West Grove, Pa.). After 45 min the mice are sacrificed within a $CO_2$ chamber. Blood is drawn via cardiac puncture (0.3 mL) (1 cc 25 g Syringes, Sherwood, St. Louis, Mo.) and transferred into a 15 mL conical vial (Nalge/Nunc International, Denmark). Blood is immediately fixed with 6.0 mL of BD Phosflow Lyse/Fix Buffer (BD Bioscience, San Jose, Calif.), inverted 3×'s and placed in 37° C. water bath. Half of the spleen is removed and transferred to an eppendorf tube containing 0.5 mL of PBS (Invitrogen Corp, Grand Island, N.Y.). The spleen is crushed using a tissue grinder (Pellet Pestle, Kimble/Kontes, Vineland, N.J.) and immediately fixed with 6.0 mL of BD Phosflow Lyse/Fix buffer, inverted 3×'s and placed in 37° C. water bath. Once tissues have been collected the mouse is cervically-dislocated and carcass to disposed. After 15 min, the 15 mL conical vials are removed from the 37° C. water bath and placed on ice until tissues are further processed. Crushed spleens are filtered through a 70 μm cell strainer (BD Bioscience, Bedford, Mass.) into another 15 mL conical vial and washed with 9 mL of PBS. Splenocytes and blood are spun @ 2,000 rpms for 10 min (cold) and buffer is aspirated. Cells are resuspended in 2.0 mL of cold (−20° C.) 90% MeOH (Mallinckrodt Chemicals, Phillipsburg, N.J.). MeOH is slowly added while conical vial is rapidly vortexed. Tissues are then stored at −20° C. until cells can be stained for FACS analysis.

Multi-Dose TNP Immunization

Blood was collected by retro-orbital eye bleeds from 7-8 week old BALB/c female mice (Charles River Labs.) at day 0 before immunization. Blood was allowed to clot for 30 min and spun at 10,000 rpm in serum microtainer tubes (Becton Dickinson) for 10 min. Sera were collected, aliquoted in Matrix tubes (Matrix Tech. Corp.) and stored at −70° C. until ELISA was performed. Mice were given compound orally before immunization and at subsequent time periods based on the life of the molecule. Mice were then immunized with either 50 μg of TNP-LPS (Biosearch Tech., #T-5065), 50 μg of TNP-Ficoll (Biosearch Tech., #F-1300), or 100 μg of TNP-KLH (Biosearch Tech., #T-5060) plus 1% alum (Brenntag, #3501) in PBS. TNP-KLH plus alum solution was prepared by gently inverting the mixture 3-5 times every 10 min for 1 h before immunization. On day 5, post-last treatment, mice were $CO_2$ sacrificed and cardiac punctured. Blood was allowed to clot for 30 min and spun at 10,000 rpm in serum microtainer tubes for 10 min. Sera were collected, aliquoted in Matrix tubes, and stored at −70° C. until further analysis was performed. TNP-specific IgG1, IgG2a, IgG3 and IgM levels in the sera were then measured via ELISA. TNP-BSA (Biosearch Tech., #T-5050) was used to capture the TNP-specific antibodies. TNP-BSA (10 μg/mL) was used to coat 384-well ELISA plates (Corning Costar) overnight. Plates were then washed and blocked for 1 h using 10% BSA ELISA Block solution (KPL). After blocking, ELISA plates were washed and sera samples/standards were serially diluted and allowed to bind to the plates for 1 h. Plates were washed and Ig-HRP conjugated secondary antibodies (goat anti-mouse IgG1, Southern Biotech #1070-05, goat anti-mouse IgG2a, Southern Biotech #1080-05, goat anti-mouse IgM, Southern Biotech #1020-05, goat anti-mouse IgG3, Southern Biotech #1100-05) were diluted at 1:5000 and incubated on the plates for 1 h. TMB peroxidase solution (SureBlue Reserve TMB from KPL) was used to visualize the antibodies. Plates were washed and samples were allowed to develop in the TMB solution approximately 5-20 min depending on the Ig analyzed. The reaction was stopped with 2M sulfuric acid and plates were read at an OD of 450 nm.

For the treatment of PI3Kδ-mediated-diseases, such as rheumatoid arthritis, ankylosing spondylitis, osteoarthritis, psoriatic arthritis, psoriasis, inflammatory diseases, and autoimmune diseases, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, rheumatoid arthritis, ankylosing spondylitis, osteoarthritis, psoriatic arthritis, psoriasis, inflammatory diseases, and autoimmune diseases and the like.

The dosage regimen for treating PI3Kδ-mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aq or oleaginous suspensions, may be formulated according to the known are using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulfuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxyethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulfuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$-$C_4$)-alkyloxy)ethyl, for example, methoxyethyl, ethoxyethyl, propoxyethyl, iso-propoxyethyl, etc.; 2-oxo-1,3-dioxolen-4-ylmethyl groups, such as 5-methyl-2-oxo-1,3dioxolen-4-ylmethyl, etc.; $C_1$-$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as polymorphs, solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

I claim:
1. A compound having the structure:

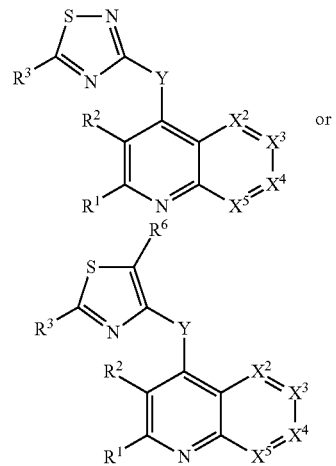

or any pharmaceutically-acceptable salt thereof, wherein:
$X^2$ is $C(R^4)$ or N;
$X^3$ is $C(R^5)$ or N;
$X^4$ is $C(R^5)$ or N;
$X^5$ is $C(R^4)$ or N; wherein no more than two of $X^2$, $X^3$, $X^4$ and $X^5$ are N;
Y is $NR^7$, $CR^aR^a$, S or O;
n is 0, 1, 2 or 3;
$R^1$ is selected from H, halo, $C_{1-6}$alk, $C_{1-4}$haloalk, cyano, nitro, —C(=O)$R^a$, —C(=O)O$R^a$, —C(=O)N$R^aR^a$, —C(=N$R^a$)N$R^aR^a$, —O$R^a$, —OC(=O)$R^a$, —OC(=O)N$R^aR^a$, —OC(=O)N($R^a$)S(=O)$_2R^a$, —O$C_{2-6}$alkN$R^aR^a$, —O$C_{2-6}$alkO$R^a$, —S$R^a$, —S(=O)$R^a$, —S(=O)$_2R^a$, —S(=O)$_2$N$R^aR^a$, —S(=O)$_2$N($R^a$)C(=O)$R^a$, —S(=O)$_2$N($R^a$)C(=O)O$R^a$, —S(=O)$_2$N($R^a$)C(=O)N$R^aR^a$, —N$R^aR^a$, —N($R^a$)C(=O)$R^a$, —N($R^a$)C(=O)O$R^a$, —N($R^a$)C(=O)N$R^aR^a$, —N($R^a$)C(=N$R^a$)N$R^aR^a$, —N($R^a$)S(=O)$_2R^a$, —N($R^a$)S(=O)$_2$N$R^aR^a$, —N$R^aC_{2-6}$alkN$R^aR^a$, —N$R^aC_{2-6}$alkO$R^a$, —N$R^aC_{2-6}$ alkCO$_2R^a$, —N$R^aC_{2-6}$alkSO$_2R^b$, —CH$_2$C(=O)$R^a$, —CH$_2$C(=O)O$R^a$, —CH$_2$C(=O)N$R^aR^a$, —CH$_2$C(=N$R^a$)N$R^aR^a$, —CH$_2$O$R^a$, —CH$_2$OC(=O)$R^a$, —CH$_2$OC(=O)N$R^aR^a$, —CH$_2$OC(=O)N($R^a$)S(=O)$_2R^a$, —CH$_2$O$C_{2-6}$alkN$R^aR^a$, —CH$_2$O$C_{2-6}$ alkO$R^a$, —CH$_2$S$R^a$, —CH$_2$S(=O)$R^a$, —CH$_2$S(=O)$_2R^b$, —CH$_2$S(=O)$_2$N$R^aR^a$, —CH$_2$S(=O)$_2$N($R^a$)C(=O)$R^a$, —CH$_2$S(=O)$_2$N($R^a$)C(=O)O$R^a$, —CH$_2$S(=O)$_2$N($R^a$)C(=O)N$R^aR^a$, —CH$_2$N$R^aR^a$, —CH$_2$N($R^a$)C(=O)

R$^a$, —CH$_2$N(R$^a$)C(=O)OR$^a$, —CH$_2$N(R$^a$)C(=O)NR$^a$R$^a$, —CH$_2$N(R$^a$)C(=NR$^a$)NR$^a$R$^a$, —CH$_2$N(R$^a$)S(=O)$_2$R$^a$, —CH$_2$N(R$^a$)S(=O)$_2$NR$^a$R$^a$, —CH$_2$NR$^a$C$_{2-6}$alkNR$^a$R$^a$, —CH$_2$NR$^a$C$_{2-6}$alkOR$^a$, —CH$_2$NR$^a$C$_{2-6}$alkCO$_2$R$^a$ and —CH$_2$NR$^a$C$_{2-6}$alkSO$_2$R$^b$; or R$^1$ is a direct-bonded, C$_{1-4}$alk-linked, OC$_{1-2}$alk-linked, C$_{1-2}$alkO-linked, N(R$^a$)-linked or O-linked saturated, partially-saturated or unsaturated 3-, 4-, 5-, 6- or 7-membered monocyclic or 8-, 9-, 10- or 11-membered bicyclic ring containing 0, 1, 2, 3 or 4 atoms selected from N, O and S, but containing no more than one O or S atom, substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$, wherein the available carbon atoms of the ring are additionally substituted by 0, 1 or 2 oxo or thioxo groups, and wherein the ring is additionally substituted by 0 or 1 directly bonded, SO$_2$ linked, C(=O) linked or CH$_2$ linked group selected from phenyl, pyridyl, pyrimidyl, morpholino, piperazinyl, piperadinyl, pyrrolidinyl, cyclopentyl, cyclohexyl all of which are further substituted by 0, 1, 2 or 3 groups selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —SR$^a$, —S(=O)R$^a$, —S(=O)$_2$R$^a$, —S(=O)$_2$NR$^a$R$^a$, —NR$^a$R$^a$, and —N(R$^a$)C(=O)R$^a$;

R$^2$ is selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^3$ is selected from a saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 R$^2$ substituents, and the ring is additionally substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^3$ is selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^4$ is, independently, in each instance, H, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk, C(=O)NH$_2$, C(=O)NHC$_{1-4}$alk, C(=O)N(C$_{1-4}$alk)C$_{1-4}$alk, N(H)C(=O)C$_{1-4}$alk, N(C$_{1-4}$alk)C(=O)C$_{1-4}$alk, C$_{1-4}$haloalk or an unsaturated 5-, 6- or 7-membered monocyclic ring containing 0, 1, 2, 3 or 4 atoms selected from N, O and S, but containing no more than one O or S, substituted by 0, 1 or 2 substituents selected from halo, C$_{1-4}$alk, C$_{1-3}$haloalk, —OC$_{1-4}$alk, —NH$_2$, —NHC$_{1-4}$alk, —N(C$_{1-4}$alk)C$_{1-4}$alk;

R$^5$ is, independently, in each instance, H, halo, nitro, cyano, C$_{1-4}$alk, OC$_{1-4}$alk, OC$_{1-4}$haloalk, NHC$_{1-4}$alk, N(C$_{1-4}$alk)C$_{1-4}$alk or C$_{1-4}$haloalk;

R$^6$ is selected from saturated, partially-saturated or unsaturated 5-, 6- or 7-membered monocyclic or 8-, 9-, 10- or 11-membered bicyclic ring containing 0, 1, 2, 3 or 4 atoms selected from N, O and S, but containing no more than one O or S, wherein the available carbon atoms of the ring are substituted by 0, 1 or 2 oxo or thioxo groups, wherein the ring is substituted by 0 or 1 R$^2$ substituents, and the ring is additionally substituted by 0, 1, 2 or 3 substituents independently selected from halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$; or R$^6$ is selected from H, halo, C$_{1-6}$alk, C$_{1-4}$haloalk, cyano, nitro, —C(=O)R$^a$, —C(=O)OR$^a$, —C(=O)NR$^a$R$^a$, —C(=NR$^a$)NR$^a$R$^a$, —OR$^a$, —OC(=O)R$^a$, —OC(=O)NR$^a$R$^a$, —OC(=O)N(R$^a$)S(=O)$_2$R$^a$, —OC$_{2-6}$alkNR$^a$R$^a$, —OC$_{2-6}$alkOR$^a$, —SR$^a$, —S(=O)R$^a$, —S(=O)$_2$R$^a$, —S(=O)$_2$NR$^a$R$^a$, —S(=O)$_2$N(R$^a$)C(=O)R$^a$, —S(=O)$_2$N(R$^a$)C(=O)OR$^a$, —S(=O)$_2$N(R$^a$)C(=O)NR$^a$R$^a$, —NR$^a$R$^a$, —N(R$^a$)C(=O)R$^a$, —N(R$^a$)C(=O)OR$^a$, —N(R$^a$)C(=O)NR$^a$R$^a$, —N(R$^a$)C(=NR$^a$)NR$^a$R$^a$, —N(R$^a$)S(=O)$_2$R$^a$, —N(R$^a$)S(=O)$_2$NR$^a$R$^a$, —NR$^a$C$_{2-6}$alkNR$^a$R$^a$ and —NR$^a$C$_{2-6}$alkOR$^a$;

R$^7$ is H, C$_{1-6}$alk, —C(=O)N(R$^a$)R$^a$, —C(=O)R$^b$ or C$_{1-4}$haloalk;

R$^a$ is independently, at each instance, H or R$^b$; and

R$^b$ is independently, at each instance, phenyl, benzyl or C$_{1-6}$alk, the phenyl, benzyl and C$_{1-6}$alk being substituted by 0, 1, 2 or 3 substituents selected from halo, $C_{1-4}$alk, $C_{1-3}$haloalk, $-OC_{1-4}$alk, $-NH_2$, $-NHC_{1-4}$alk, $-N(C_{1-4}$alk$)C_{1-4}$alk.

2. A pharmaceutical composition comprising a compound according to claim 1 and a pharmaceutically-acceptable diluent or carrier.

* * * * *